(12) United States Patent
Bendele et al.

(10) Patent No.: US 8,337,755 B2
(45) Date of Patent: Dec. 25, 2012

(54) OPERATOR INDEPENDENT PROGRAMMABLE SAMPLE PREPARATION AND ANALYSIS SYSTEM

(75) Inventors: Teresa Bendele, Doylestown, PA (US); Thomas Harbart, North Royalton, OH (US); Dave Howard, North Ridgeville, OH (US); Michael Kagan, Doylestown, PA (US); Douglas Keene, North Wales, PA (US); Dave Lapeus, Medina, OH (US); Jared Mayes, Ambler, PA (US); Douglas Paynter, Doylestown, PA (US); Jerry Prohaska, Huntingdon Valley, PA (US); Herman Rutner, Hatboro, PA (US)

(73) Assignee: Veridex, LLC, Raritan, NJ (US)

( * ) Notice: Subject to any disclaimer, the term of this patent is extended or adjusted under 35 U.S.C. 154(b) by 1034 days.

(21) Appl. No.: 11/374,623

(22) Filed: Mar. 13, 2006

(65) Prior Publication Data

US 2007/0212698 A1     Sep. 13, 2007

(51) Int. Cl.
*B01L 3/02* (2006.01)
(52) U.S. Cl. ............ 422/104; 422/63; 422/64; 422/102; 436/526; 436/43; 436/47; 206/563
(58) Field of Classification Search ................... 422/104, 422/63, 64, 102; 436/526, 43, 47; 206/563
See application file for complete search history.

(56) References Cited

U.S. PATENT DOCUMENTS

| | | | |
|---|---|---|---|
| 5,186,827 A | 2/1993 | Liberti et al. | |
| 5,466,574 A | 11/1995 | Liberti et al. | |
| 5,507,410 A | 4/1996 | Clark | |
| 5,698,271 A | 12/1997 | Liberti et al. | |
| 5,985,153 A | 11/1999 | Dolan et al. | |
| 6,013,188 A | 1/2000 | Terstappen et al. | |
| 6,046,585 A | 4/2000 | Simmonds | |
| 6,120,856 A | 9/2000 | Liberti et al. | |
| 6,136,182 A | 10/2000 | Dolan et al. | |
| 6,190,617 B1 * | 2/2001 | Clark et al. | 422/104 |

(Continued)

FOREIGN PATENT DOCUMENTS

JP     2002323500     11/2002

(Continued)

OTHER PUBLICATIONS

Canadian Search Report dated Mar. 23, 2012 for corresponding Patent Application No. CA2539108.

(Continued)

*Primary Examiner* — Mark Shibuya
*Assistant Examiner* — Pensee Do
(74) *Attorney, Agent, or Firm* — Rudy T. Hope

(57) ABSTRACT

The present invention provides a protocol and apparatus for enriching circulating tumor cells and other rare cells from blood, including debris and other components, from samples with high precision and at high throughput rates. This invention discloses an improved processing system from previously described semi-automated sample processing. The system further reduces operator intervention and hands-on time from prior systems. While this system has general utility in processing diverse materials, the system is configured for sample processing of biological specimens to provide an enriched fraction suitable for detection, enumeration and identification of target cells by appropriate analytical methodologies. The presence and quantities of such target cells in a sample specimen can utilized for screening and detection in disease such as cancer, assessing early stage pre-metastatic cancer, monitoring for disease remission in response to therapy and selection of more effective dose regimens or alternative therapies in case of relapse.

13 Claims, 9 Drawing Sheets

U.S. PATENT DOCUMENTS

| | | |
|---|---|---|
| 6,350,613 B1 | 2/2002 | Wardlaw et al. |
| 6,365,362 B1 | 4/2002 | Terstappen et al. |
| 6,551,843 B1 | 4/2003 | Rao et al. |
| 6,620,627 B1 | 9/2003 | Liberti et al. |
| 6,623,982 B1 | 9/2003 | Liberti et al. |
| 6,790,366 B2 | 9/2004 | Terstappen et al. |
| 6,855,542 B2 * | 2/2005 | DiMilla et al. .............. 435/289.1 |
| 6,861,259 B2 | 3/2005 | Columbus |
| 7,011,794 B2 | 3/2006 | Kagan et al. |
| 7,863,012 B2 | 1/2011 | Rao et al. |
| 2001/0007312 A1 | 7/2001 | Siddiqi |
| 2002/0172987 A1* | 11/2002 | Terstappen et al. .......... 435/7.23 |
| 2003/0203507 A1 | 10/2003 | Liberti et al. |
| 2005/0181353 A1 | 8/2005 | Rao et al. |
| 2006/0207322 A1* | 9/2006 | Krufka et al. ............... 73/304 C |

FOREIGN PATENT DOCUMENTS

| | | |
|---|---|---|
| WO | WO 99/41613 A1 | 8/1999 |
| WO | WO 02/077604 A2 | 10/2002 |
| WO | WO 03/019141 A2 | 3/2003 |

OTHER PUBLICATIONS

Supplementary European Search Report dated Oct. 20, 2011 for corresponding Patent Application No. EP04784320.

* cited by examiner

Front View of System Layout

Top View of System Layout

Panel-A

Panel-B

OPERATOR INDEPENDENT PROGRAMMABLE SAMPLE PREPARATION AND ANALYSIS SYSTEM

PRIORITY

This application claims the benefit of U.S. provisional application 60/503,754, filed on Sep. 18, 2003.

BACKGROUND

1. Field of the Invention

This invention relates generally to the field of automated sample processing, and more particularly to the isolation of rare cells from body fluids by an automated device for further analysis as it relates to the diagnosing, monitoring and managing of specific diseases, particularly cancer.

2. Background Art

The principal methodology and apparatus of the present invention stems from prior art assessing the detection and enumeration of cells in biological samples. These biological samples include, for example, blood, lymphatic fluid, or cerebral spinal fluid. A biological sample can also include buffer with spiked cultured cells, used as a control.

Manual methods for the isolation and quantification of rare cells of in peripheral blood and other biological matrices have been published and are well known in the art. However, to create sensitive, reproducible and high throughput testing protocols suitable for clinical diagnosis, an automated process is necessary.

It is well known that, for highly complex laboratory procedures, the root cause of erroneous results can frequently be traced to the cumulative effects of systematic or random pre-analytical errors, i.e. errors occurring during sample preparation or pre-processing stages rather than to the analytical method itself. Pre-analytical errors may manifest as variations due to technique-sensitive process steps as well as normal random or systematic variations from operator to operator. Sample preparation, specifically cell enrichment, is an example of a pre-analytical process which, when performed inconsistently, will manifest itself in high variability of assay results. Hence, automating such pre-analytical steps would minimize variability and result in more consistent analytical results.

Cell enrichment techniques for the isolation of rare cells vary widely and involve a variety of manual techniques to selectively isolate target cells for analysis. Centrifugation, with or without density gradients, is a common method employed. However, centrifugation does not easily lend itself to automation without the addition of complex robotic handling of sample tubes, computer-controlled centrifuges, etc. Often times, manual wash steps also involving centrifugation steps follow these procedures. If an approach were taken to automate all of these manual procedures directly, the end result would be a highly complex and expensive system that would mimic the manual processes performed by a skilled operator.

Magnetic separation of immuno-magnetically labeled target entities directly from the specimen is the ideal mode, but frequently inefficient if the target entity is a minor constituent in a complex mixture. Pre-purification by centrifugation or gradient separations followed by magnetic labeling and collection may be necessary in such cases. Again, these approaches do not lend themselves to facile automation without the addition of complex robotic handling systems for sample tubes, computer-controlled centrifuges, etc. Manual wash steps also involving centrifugation steps often follow these procedures. Again, direct automation of these manual procedures would result in a highly complex and expensive robotic system mimicking a manual process where every process step increases the risk of cell loss.

Several companies offer semi-automated systems specifically adapted to cell sorting or selection with application to cancer diagnostics and treatment. Miltenyi Biotech, Germany, has developed the autoMACS system, a semi-automated bench top magnetic cell sorter for collecting magnetically labeled target cells that are subsequently further sorted or fractionated on a flow cytometer into various cell populations including presumed target cells. However, the AutoMACS requires an enriched fraction prepared by manual pre-purification of complex specimens, e.g. blood, to remove most of the non-target cells. Flow cytometry also detects fluor-labeled particulate events of certain sizes not cells, i.e. without morphological confirmation of the identity of the detected events as target cells. U.S. Pat. No. 6,046,585, issued to Quantum Design, San Diego, discloses methods and apparatus for sensing and measuring small quantities of magnetic particles bound to target entities including cells; however, these entities are not considered rare.

The semi-automated method and apparatus, previously described (U.S. patent application Ser. No 10/081,996), is primarily designed to enrich circulating cells from blood and other specimens with a greater precision than attainable with the aforementioned manual methods. This is accomplished primarily by replacing imprecise manual steps such as vortex/mixing and quantitative fluid transfers with magnetic enrichment and magnetic washing, thus removing the steps typically involved in centrifugal density gradient separation. Aspiration steps normally performed manually were automated as well. The procedure required operator intervention periodically throughout the process, thus leading to variable process timing. While the system has general utility in sample processing of diverse materials, particularly biological specimens in a research setting, a more automated system incorporating a system of checks to prevent reagent or sample loss would greatly improve preparation and increase the integrity of the sample for clinical use.

The disclosed apparatus is a substantial improvement to the semi-automated detection device of Ser. No. 10/081,996. In the present application, the operator interaction during processing is eliminated, thus reducing associated errors. Sample preparation time is reduced and standardized with more precise control of individual processing steps. The improved system provides an enriched fraction suitable for detection, enumeration and identification of target cells by various analytical methodologies. The presence and quantities of such target cells in a sample specimen can be utilized for screening and detection in multiple types of diseases such as, but not limited to, metastatic cancer and cardiovascular disorders. Further, the isolation and analysis of these target cells has diagnostic importance in assessing multiple aspects of a disease, such as for example in cancer with early stage pre-metastatic cancer, monitoring for response to therapy and selection of more effective dose regimens or alternative therapies.

SUMMARY OF THE INVENTION

The present invention provides apparatus and methods for an instrumental protocol to enrich circulating cells, cell components, and/or target entities from blood and other specimens which is more rapid, completely automated and independent from hands-on operation in prior semi-automatic analysis methods. Thus, the invention eliminates most user originating errors and reduces assay variability. The invention discloses a novel automated sample processing system to prepare a sample for analysis, which improves upon a prior application (U.S. patent application Ser. No. 10/081,996). This is accomplished, in part, with computer controlled fluidic control, motion control, error detection, and recovery.

Inventive aspects of the present application are primarily embodied in the AutoPrep System. For this system, sample processing involves two sub-processes. The first occurs prior to starting a batch run, ensuring that all required components are present. The system assesses inventory of required items based upon the user requesting to process a number of samples. Through an integral data storage device in the test specific reagent carrier (iButton, Dallas semiconductor) and instrument sensors, the system assesses the inventory of certain items required for processing a batch of samples. The inventory includes, but not limited to, sample tubes, System fluid, Liquid waste, reagents, and the sample cartridge (77) apparatus (U.S. patent application Ser. Nos. 10/074,900 and 10/303,309). During the first process, the instrument locates the height of the red cell layer in each tube of centrifuged blood and aspirates the plasma aspirated to a pre-programmed distance above the red cell layer. This process must be completed successfully for the sample to be processed further.

The second of 2 processes enriches the target cells in the aspirated samples as determined by the reagent pack and associated protocol software. Enrichment is accomplished by sequentially reducing the amount of fluid at each process step until a 320 uL sample volume is achieved. The samples are cycled through a series of 9 discrete stations. The prepared samples are subjected to a series of steps that results in an enriched rare cell fraction for each sample in the batch. Station 1 dispenses the cell capture reagents to bind to targets, identified in the reagent pack. Station 2 and 3 perform magnetic incubations that allow the coated magnetic particles to travel within the sample in the presence of a magnetic field and bind to target cells. Station 3 begins the separation process by magnetically pulling the captured cells to the inside wall of the sample tube. Station 4 completes the magnetic separation by collecting the captured cells and unbound ferrofluid at a specific location within the tube, aspirating all non-magnetic constituents in the sample tube, re-suspending the magnetically labeled fraction with a stream of fluid. Station 5 performs a magnetic wash with the addition of permeabilization reagent, disassociating reagent and the addition of appropriate staining reagents (membrane, cell nucleus, etc.). Station 6 continues with staining and incubation. Station 7 performs a additional magnetic wash and involves the removal of the staining reagent. In Station 8, the cells are allowed to settle in preparation for unbound ferrofluid fractionation (i.e. separating unbound ferrofluid from cells bound with ferrofluid). This step is necessary to reduce the interference of the unbound ferrofluid with fluorescence measurements. Station 9 reduces of the unbound ferrofluid present, dispenses a cell preservative in buffer solution, such as that described in U.S. patent application Ser. No. 10/780,349, and transfers the enriched cells in solution to a sample cartridge (77) for analysis (U.S. application Ser. Nos. 10/074,900 and 10/303,309).

Within the two discussed processes, motion control elements have been developed to ensure accurate and precise positioning of the probes, sample tubes, and reagents during operation. A magnetic shuttle device allows for computer-controlled application of magnetic field gradients to the sample at the designated steps in the process. A tube rotation system rotates the tube to facilitate all of the magnetic incubations and separations required by the process.

The system described by the invention has a series of sensors to verify that all samples are processed correctly. These processing steps include, but not limited to, plasma aspiration, magnetic separations, post-separation aspirations, reagent additions, expected interim sample volumes, and the final transfer to the sample cartridge (77).

Finally, the system incorporates several provisions within the computer interface, which are integral in providing automated and rapid sample preparation. A cleaning routine and associated fluid has also been included to allow unattended maintenance with minimum operator interaction.

Thus, this automated rare cell enrichment processor improves upon process efficiency, reduces operator error, and improves the overall precision of manual or semi-automated processes described earlier. The invention discloses a novel automated sample system with general utility in precise sample processing. In particular, the system embodies a configuration for reliable and efficient sample processing of biological specimens such as blood and provides and enriched fraction of cells suitable for detecting rare target cells. Enumeration and identification of these target cells is accomplished by specific analytical methods such as, but not limited to, imaging systems described in U.S. Pat. Nos. 6,365,362 and 6,013,188. Thus, the present invention embodies the use of the above described device in assessing the existence and quantification of such target cells in a sample specimen. While all circulating cell types are contemplated in the use of the present invention, this device can be utilized for screening and detection in early stage pre-metastatic cancer, monitoring response to therapy and selection of more effective dose regimens or alternative therapies. Epithelial cells, endothelial cells, bacterial and fungal cells are also considered in the present invention. Further, the present invention is useful in assessing the existence and quantification of such cell constituents as components and circulating debris.

DETAILED DESCRIPTION OF THE INVENTION

Figure 1:
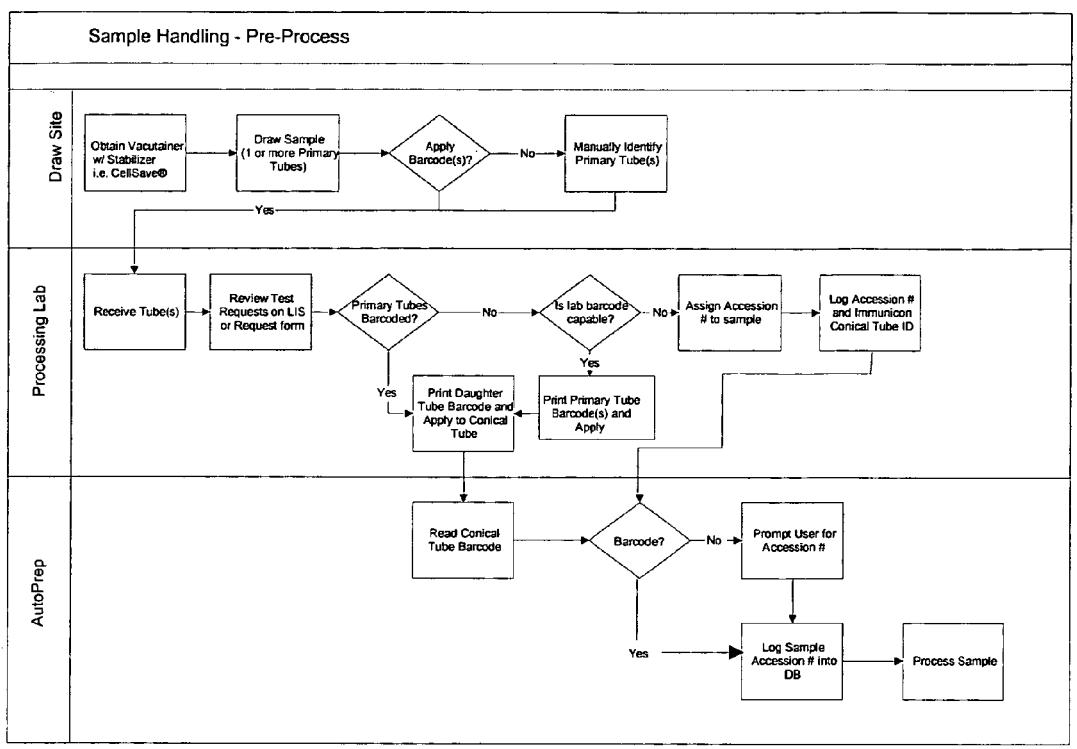
FIG. 1: Flow chart for Sample Pre-processing. Shown are the series of steps from blood draw to presentation of the sample for batch processing.

Tumor cells are often present in blood of carcinoma patients at very low frequency (<10 cells per ml) and may provide clinically useful information. However, the laborious procedures required to detect and quantify the presence of circulating tumor cells introduce a high level of variability in the results. The system of this invention aids in processing and analysis of 4 to 30 ml blood samples for tumor cells of epithelial origin and other rare cell fractions.

Target cells are labeled and separated from blood by magnetic means and the captured cells are fluorescently labeled to permit detection and differentiation from non-target cells.

The apparatus of this invention eliminates a substantial number of user required steps, and produces a 320 ul liquid sample that is placed in a suitable analysis chamber (for example, but not limited to, the chamber described in U.S. Ser. No. 10/074,900) for use in the image analysis systems. For example in the CellSpotter®, the chamber is placed into a magnetic device that directs magnetically labeled cells in the sample to an optically clear planar surface of the chamber. The magnetic device and chamber are then placed on a fluorescence microscope equipped with a computer controlled filter selector and digitally controlled X-Y-Z stage as exemplified in the CellTracks® automated fluorescent imaging instrumentation.

The present invention is an automated diagnostic system comprising, in part, steps a to f of the following sequence, all performed with the disclosed apparatus.
 a. detection of the location of the plasma—red cell transition in the sample,
 b. removal of plasma
 c. adding magnetic particles coated with binders recognizing specific determinants on the targets for the purpose of forming magnetically labeled targets,
 d. incubation and selectively collecting and thereby separating the labeled target cells magnetically from undesirable non-targets and matrix components and removing said non-target cells,
 e. selectively staining the collected targets and residual non-targets with multiple fluorophores to permit differentiation of targets from non-targets,
 f. magnetically washing the stained targets,
 g. fractionate bound cells from unbound ferrofluid,
 h. transferring the collected labeled targets to an analysis device (e.g. a sample chamber for analysis), and
 i. analyzing the collected cells by appropriate analytical methods for the purpose of characterizing, identifying and enumerating the targets present in the specimen.

The last three steps (steps g to i) may be performed in a novel sample chamber (U.S. Ser. No. 10/074,900 and U.S. Pat. No. 10,303,309), incorporated in the following patents and co-pending applications; U.S. Pat. Nos. 5,186,827, 5,698,271, 6,120,856, 6,551,843, U.S. Ser. Nos. 09/702,188, 10/449,355, or on the CellTracks system (U.S. Pat. Nos. 5,985,153; 6,013,188; 6,136,182 and pending application Ser. No. 10/602,979).

The present invention is an improvement in the methodology, apparatus, and software previously described for the automated technique-sensitive steps in cell enrichment (Ser. No. 10/081,996). This improvement provides a further reduction in the loss of target cells, reduced assay variability, improved process reliability and programming for efficient and effective implementation.

Preparation Prior to a Batch Run

Preparation of blood samples begins with the collection of the sample (FIG. 1). Individual sample are properly labeled, using barcode labels or other means of unique sample identification.

Improvements in the basic steps involved in processing a sample and the approaches for handling specific error conditions are outlined below. These improvements apply to priming and washing probes, reagent additions, post-separation aspirations and magnetic separation methods that are common to several stations in the automated process of this invention. Any errors encountered during the batch preparation are reported to the operator for remediation before the preparation process can continue. When processing samples obtained from patients, individual sample losses from system failure will require the patient blood to be redrawn. This condition imposes upon the patient to submit a new sample and delays the process of providing the clinician with a result. Minimizing the probability of a failed sample is addressed, in part, with the improved aspects of the present invention.

A sample can be incompletely processed if the process is stopped due to lack of a necessary reagent or device (i.e. cartridge (77)) required for processing. For this reason, one of the embodiments behind the current system is that it is able to assess the inventory of these items prior to attempting to process a sample. For example the System fluid level, the liquid waste container level, reagents, and sample cartridges (77) are inventory items that are checked to avoid downstream sample processing errors.

Figure 2:
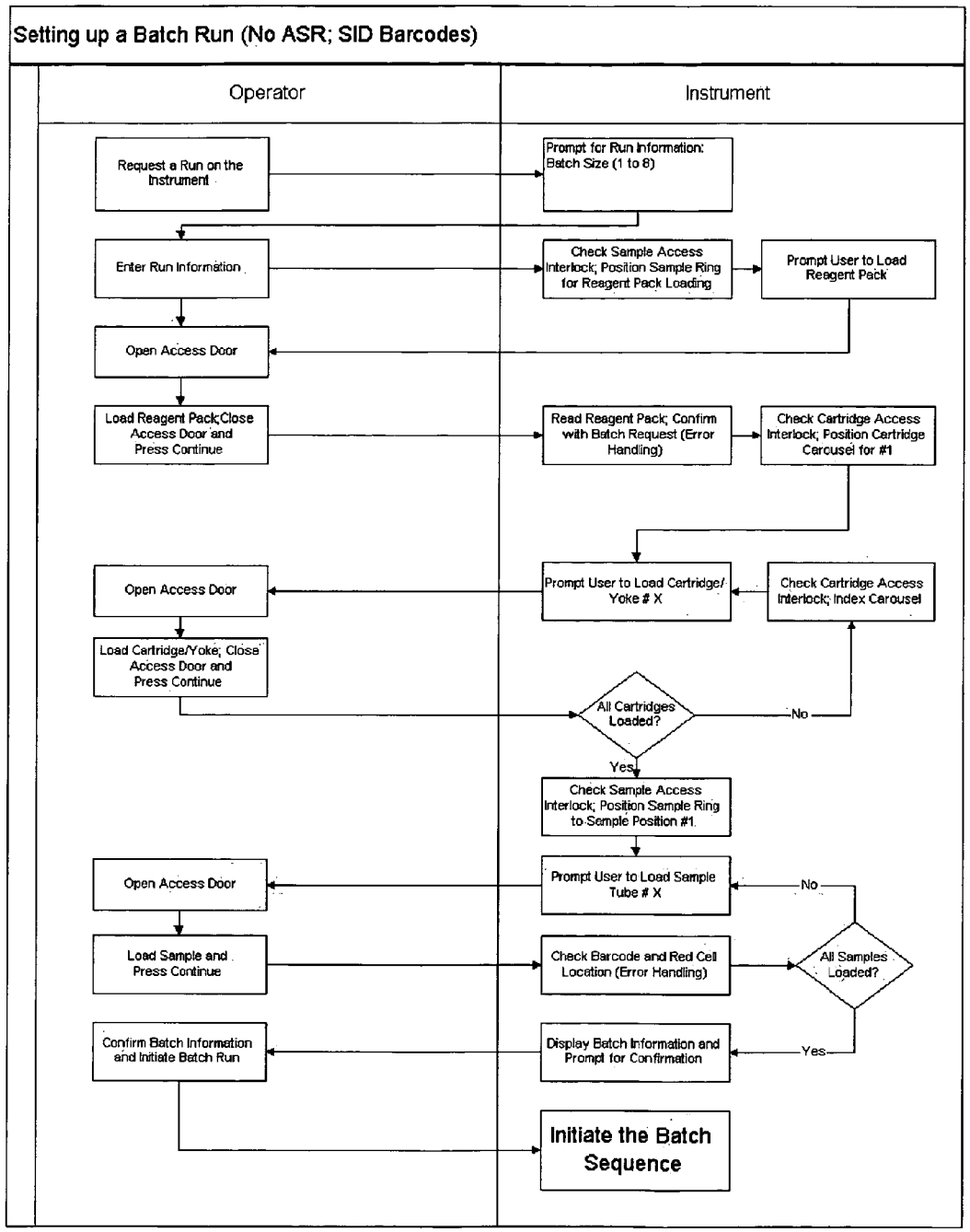
FIG. 2: Flow Chart Depicting the Steps Involved in Setting Up a Batch Run.

Inventory assessment is accomplished through several means such as, but not limited to, data storage devices and sensor subsystems (FIG. 2). Before beginning a batch run, the operator is required to load the sample tube with either a barcode identifying the sample ID or a manually entered unique accession number. The instrument will move the tube to the barcode read station and attempt to read the barcode. The reading occurs immediately after the operator confirms that the tube is loaded, allowing for corrections before the next tube is loaded. If the barcode is not readable or not present, the instrument will notify the operator and present the tube for re-alignment or re-labeling or manual entry of an accession number.

Barcode formats that are supported are one of the following; Code 128, Codabar, Interleaved 2 of 5, and Code 39.

The sample cartridge (77) is bar-coded and read to verify the cartridge (77) and each sample cartridge is loaded properly. Based upon successful reading and recording of data onto an individual cartridge data storage device (FIG. 1, lower panel), the system allows the batch process to proceed.

Figure 3:
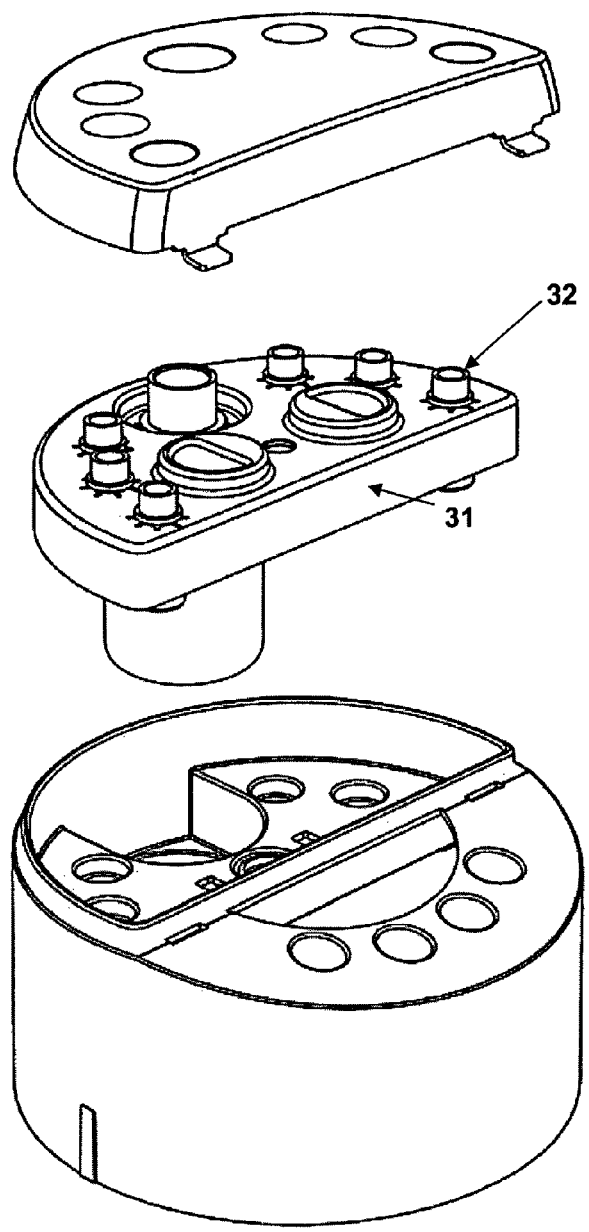
FIG. 3: Diagram of Instrument Reagent Pack and Re-useable Carrier.

The reagent pack data button is read and used to verify sufficient reagent inventory in the reagent pack exists for completion of the samples to be processed (FIG. 3). The data button (31) used in the reagent pack (32) has 16K bits of EEPROM storage and contains all relevant reagent lot, expiration dating, and inventory information required by the system.

Prior to the initiation of a batch run, the red cell layer in the sample tube is measured at Station 1. A valid red cell layer is defined in the test definition software for a specific test. For a 7.5 ml sample volume, 1.5 ml is equivalent to a 20% hematocrit and 4.5 ml is equivalent to a 60% hematocrit.

In preparation for plasma aspiration, the tube is moved to the plasma aspiration position of Station 4. The fluid level is confirmed using the Station 4 aspiration probe and an integral liquid level sensor. If the fluid is not in range, the operator is notified for corrective action. This acts as a check on the proper volume of the sample before the start of the process.

The Station 4 aspiration probe aspirates down to a preprogrammed distance above the red cell layer, as determined earlier, with all aspirations being performed on all samples as a batch prior to the start of sequential processing. The operator, prior to commencing batch sample processing, can correct errors detected by this process.

Batch Processing

Figure 4:
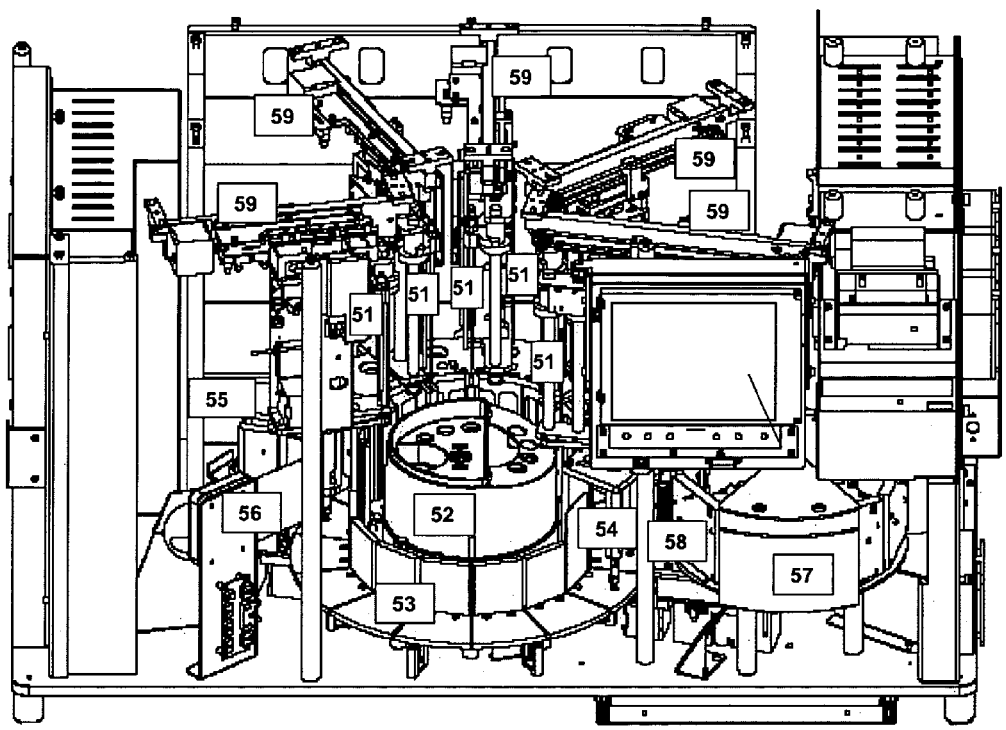
FIG. 4: Front and Top View of System Layout.
Figure 4A:
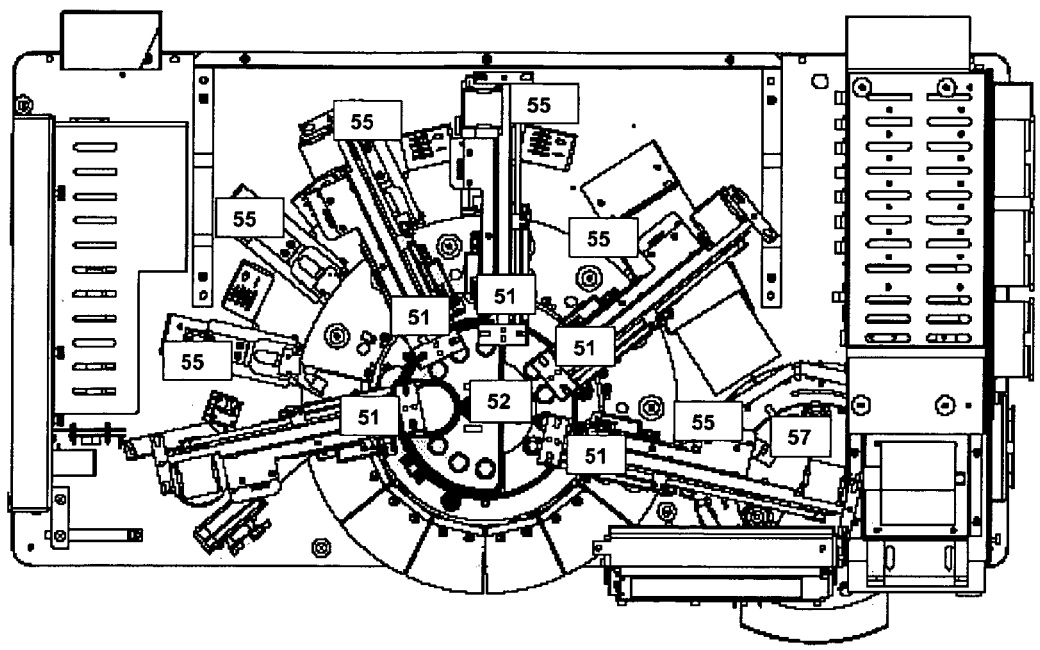

Once the pre-batch process has been completed successfully for all samples loaded, the individual batch run begins. Tubes are subjected to a series of 9 Stations for sample processing with up to 8 unique samples processed sequentially to the following protocol. A general perspective of the system layout is shown in FIG. 4 with a front and top view. With exceptions stated in the following description, each station is equipped with 2 probes; one for aspiration of waste fluid and one for reagent pickup and dispense. Each station that introduces magnetic fields to the sample is equipped with a magnet assembly and shuttle mechanism for engaging and disengaging the magnetic field with the sample.

Station 1—Reagent Addition and Mixing

At Station 1, reagents such as buffer, ferrofluid, and a capture enhancing reagent, (i.e. streptavidin) are dispensed through the reagent probe (51) (U.S. Pat. Nos. 6,623,982 and 6,620,627).

The Station 1 reagent probe (51) is used to aspirate the first reagent (i.e. buffer). The first required reagent bottle is properly positioned in the carousel (52), the fluid level found, and the reagent aspirated. This procedure is repeated for the second and third reagent bottles (i.e. ferrofluid and a capture enhancing reagent, respectively). For each subsequent aspiration, small air gaps separate each reagent as defined in the method. Similar air gaps are used in each of the subsequent station procedures requiring aspirations of multiple reagents. These air gaps reduce the possibility of cross contamination of reagents during multiple pick-up methods.

The reagent probe is sent to detect the surface of the sample using capacitive liquid level sensing. When the fluid level is found, the probe tip stays under the surface of the fluid to minimize bubble formation. The probe (51) will penetrate the initial volume of red cells to ensure that the reagents dispense adequately for the mixing of reagents and sample. The probe (51) follows the fluid level upward to minimize exposure of the outside of the probe (51) to the sample. Dispensing is followed by washes for both inside and outside the probe (51) to reduce sample carryover effects.

Station 2—Magnetic Incubation

Figure 5:
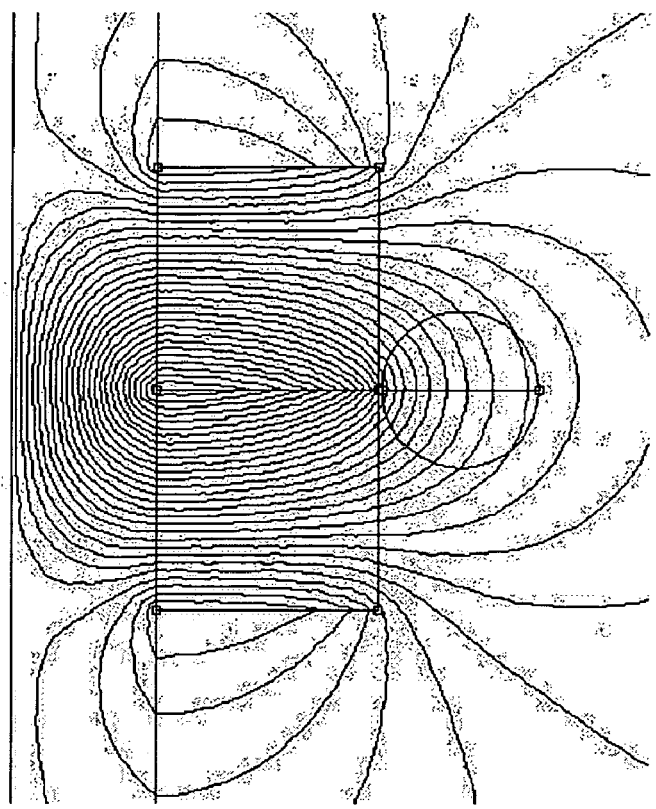
FIG. 5: The magnetic configuration for the AutoPrep magnets. Panel A depicts the field lines and contour for the 180 degree dipole magnet (Station 4, 5, 7 and 9). Panel B depicts the field lines and contour for the 70 degree tripole magnets (Station 2 and 3).
Figure 5A:
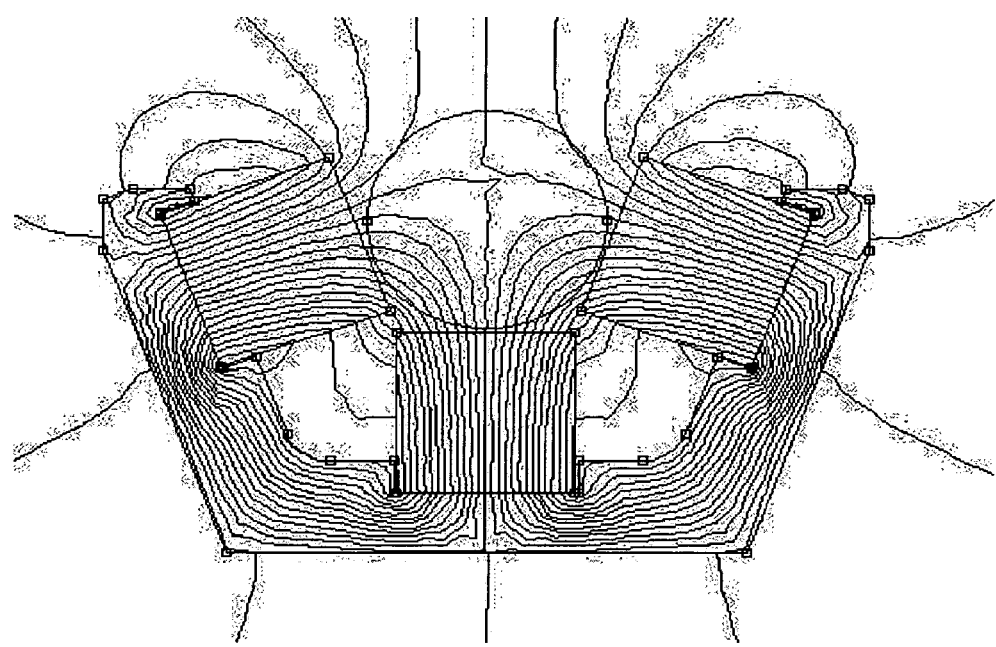

FIG. 5 (Panel B) shows the field lines and contour for the 70-degree tripole configuration of the magnets at station 2 and 3 where the objective is to maintain a sheet of particles and not a concentrated collection of either ferrofluid or cells.

Station 2 is the first of two magnetic incubation stations. The tube is placed within the magnetic field to allow the ferrofluid to travel through the sample. When sufficient time for collection has elapsed, the magnets are dis-engaged and tube rotated 180 degrees. The magnet is re-engaged and the collection process begins again. Thus, the magnetic incubation is a combination of rotating the tube and cycling the engagement of the magnets. The incubation may involve one or more cycles of tube rotations with far/near positioning of the magnets. A typical cycle is every 3 minutes and is programmable within the method for individual applications.

Station 3—Magnetic Incubation and Collection

The tube is moved to Station 3 for continuation of the magnetic incubation of the cycle is similar to that of Station 2, except that the magnetic field cycling is altered during the process to begin collecting the ferrofluid and captured cells to the side of the sample tube in preparation for Station 4. At the end of Station 3, the magnetic field is disengaged from the tube, and the tube is move to Station 4.

Station 4—Collection and Fractionation

Station 4 also involves a magnetic separation sequence of engaging the magnetic field and slowly rotating the tube. FIG. 5 (Panel A) represents the field lines and contour plot for the 180-degree dipole magnet used for this station. The purpose at this station is to collect the captured cells and unbound ferrofluid while also pulling both downward to a lower level in the sample tube and allowing for re-suspension of the cells with a 3 mL fluid stream. The original sample volume is greater than the resuspension stream at this station. Therefore, the cells and magnetic particles must be at a physical height that is consistent with the volume of the dispense volume. Because re-suspension is performed with a fluid stream, as opposed to vortexing in previously described manual methods, it is essential that the cells are located in a predictable and known location. As the sample tube is rotated against the high gradient portion of the magnet configuration, the magnetic field gradient causes the cells to locate along the high gradient area, defined by the junction of the North and South magnet poles.

Figure 6:
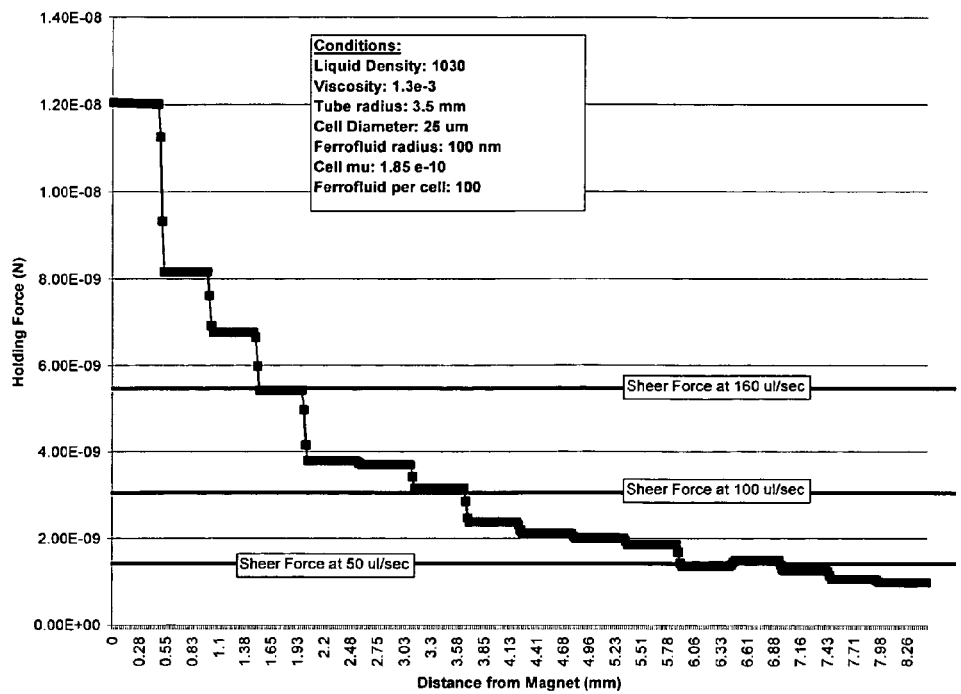
FIG. 6: Relationship between the holding force and meniscus shear force for 180 dipole configurations

Post-separation aspiration begins at the Station 4 tube when rotation is stopped. The fluid level in the tube is found. A peristaltic pump then slowly aspirates the fluid with the least amount of turbulence with the probe (51) maintaining a small and constant depth during aspiration. Careful balance between the magnetic holding force and fluid sheer forces are necessary so that rare cells are not broken or dislodged from the tube surface and aspirated to waste (see FIG. 6). When aspiration is finished, the probe (51) is raised to a position above the original sample level.

Subsequently, the post-separation aspiration is verified by using the aspirate probe (51) to find the fluid level. The fluid level should be just above the tube bottom. When confirmed, the Station 4 aspiration probe (51) is raised to a preset storage position (home).

A side port reagent probe (51) is prepared for a wash re-suspension dispense. Using a side port reagent probe (51), the wash for re-suspension dispense is completed with a 3 ml mixture of wash dilution buffer and system buffer dispensed along the conical wall of the tube to re-suspend captured cells. The reagent probe (51) is positioned above the center of the tube. After the Station 4 magnetic field is disengaged, allowing the collected cells to be resuspended with a fluid stream. Completion is followed by sample movement to Station 5.

Station 5—Cell Staining and Sample Volume Reduction

Station 5 operation consists of a magnetic wash and the addition of a ferrofluid dissociation reagent, permeabilization reagent and staining reagents. The magnetic field is engaged and the tube is rotated in order to execute the magnetic separation, similar to that of Station 4. The Station 5 magnet is shorter than that of Station 4. This causes the magnetically labeled cells to collect at a lower position within the sample tube, thus allowing resuspension of the cells with a lower dispense volume than that used at Station 4.

The Station 5 tube rotation is stopped, and the aspiration probe (51) is used to detect the fluid level in the tube providing a check for proper dispensing of Station 4 reagent volume (3 ml). The volume in the tube should be equal to the wash-dispense volume. If the fluid level is not within a predetermined range, the Station 4 reagent addition failed and an error is reported.

With the magnet engaged, the post-separation aspiration step is completed with the Station 5 aspiration probe (51). As stated above, maintaining a balance between the magnetic holding force and the fluid sheer forces are necessary to prevent damage to rare cells. The peristaltic pump slowly aspirates the fluid (typical aspiration rate is about 120 to 250 ul/sec), moving downward to maintain probe depth during aspiration as described in Station 4. When finished, the Station 5 aspiration probe (51) returns to the home position.

The probe (51) is then used again to verify that aspiration was completed successfully. For cell re-suspension, the reagent probe (51) picks up the previously described reagents and is positioned above the outer quadrant of the tube, and the magnet shuttle is disengaged. The reagent probe tip is positioned just above the outer quadrant conical surface of the sample tube which is coincident with the top of the collected cells along the tube wall.

The reagent is dispensed. Additional mixing is accomplished through a series of small aspiration/dispense cycles and small tube rotation actions while the probe is below the fluid level. This improves reagent mixing and aides in ferrofluid dissociation once the disassociation reagent (biotin) has been added (U.S. Pat. Nos. 6,623,982 and 6,620,627).

Station 6—Staining Incubation

Station 6 involves incubation for staining and de-aggregation of the magnetic particles. Here, the cells are stained.

Station 7—Magnetic Wash and Sample Volume Reduction

In Station 7, the cells undergo a magnetic wash and reagent removal. The liquid level in the sample tube is detected via capacitive level sensing. The volume of the tube is compared to an expected value. If the volume is not as expected, an error is reported to the operator. The Station 7 magnet is shorter than that of Station 5. This causes the magnetically labeled cells to collect at a lower position within the sample tube, thus allowing resuspension of the cells with a lower dispense volume than that used at Station 5.

1 ml of a protein-based buffer is picked up from the reagent pack (52) and added to the sample to dilute the reagents added at Station 5. The sample is mixed similar to the aspirate/dispense method described for Station 5.

The magnetic field is engaged and the tube rotated to execute the magnetic separation sequence, similar to that of Station 4 and 5, however, the Station 7 magnet is shorter in the vertical direction that that of Station 5. Instrument buffer and reagents are aspirated from their associated bottles.

Preparation is made for post-separation aspiration. With the aspiration probe (51), the fluid level in the tube is found. If fluid volume is not within the predetermined range, either Station 5 and/or 7 reagent additions failed and an error is reported.

Using Station 7 aspiration probe (51), the post-separation is completed. With the syringe pump specific to this station, the fluid in the tube is removed slowly by moving the probe (51) downward to maintain probe depth during aspiration. Station 7 aspiration probe (51) is raised and returned to the home position.

Post-separation aspiration verification is completed with the aspiration probe (51) to determine the fluid level to just above the tube bottom. For preparation of re-suspension dispense, the station 7 magnet is disengaged from the tube which is then rotated 180 degrees so that the magnetic particles are the furthest away from the magnet. The reagent probe (51) is positioned above the outer quadrant of the tube and above the magnetic particle pellet. The reagent probe (51) is then lowered to a position where the tip is just above the collected cells.

Using the reagent probe (51), the reagent is dispensed along the conical wall of the tube to re-suspend the captured cells. Additional mixing is accomplished through a series of small aspiration/dispense cycles and small tube rotation actions while the probe (51) is below the fluid level. This improves the reagent mixing and aids in ferrofluid disassociation. The tube is then moved to Station 8.

Station 8—Cell Settling

Station 8 allows cell settling and ferrofluid removal. Here, the cells are settling during the step in preparation for magnetic ferrofluid fractionation. This is followed by moving the tube to Station 9. The relative density of the cells with respect to the surrounding buffer causes the cells to settle at a rate of approximately 6 um/sec while the unbound and disassociated ferrofluid remains in suspension due its colloidal nature.

Station 9—Ferrofluid Fractionation and Cell Transfer

In Station 9, the unbound ferrofluid aspirated to waste and the magnetic fraction of cells transferred to the analysis cartridge (77).

The reagent is aspirated into the transfer probe (51), by positioning the required bottle at Station 9.

Magnetic separation for ferrofluid reduction is accomplished by engaging magnets to pull and hold settled cells to the side of the tube's cone portion. The magnets are engaged for a programmed amount of time to avoid collection of unbound ferrofluid. Shown in FIG. 5 (Panel A) are the field lines and contour for the 180-degree magnetic configuration used at this station. This is similar to the configuration at station 5 and 7 with smaller magnets. As with prior station magnets, the Station 9 magnets are smaller than those used at Station 7, thus reducing the vertical position of the magnetically labeled cells to allow resuspension with approximately 250 uL of fluid.

Preparation for post-separation aspiration is accomplished using the aspiration probe (51) to find the fluid level in the tube. This is a check on whether Station 7 reagent dispense process added the proper volume. The volume in the tube should be within a predetermined range. If the fluid level is not within the range, Station 7 reagent addition failed and an error is reported.

Post-separation aspiration is completed (100 ul/sec) with the aspiration probe (51) positioned at the bottom of the sample tube.

The preparation for dispense of the fixative solution (U.S. Ser. No. 10/780,349) re-suspension follows. With the magnet shuttle disengaged, the transfer probe (51) is lowered to a position where the probe tip is above the center of the tube. The re-suspension is dispensed through the transfer probe (51). Dispense of the reagent is from the center of the tube with the captured cells re-suspended. A series of aspiration/dispense cycles are performed to improve mixing and re-suspension of the cells.

For preparation for the transfer to a cartridge (77), the fluid level is found in the tube and checked for proper volume from the Station 9 dispense. The volume in the tube should be the reagent. If the fluid level is not within range, Station 9 reagent addition failed and an error is reported.

The fluid is transferred to the sample cartridge (77). Using the transfer probe (51), the entire contents of the tube are aspirated by placing the probe tip at the tube bottom while aspirating. The transfer probe (51) is moved to the vertical home position and in the X-direction to the position above the target cartridge (77). The transfer probe (51) is lowered into the cartridge (77) and the transferred solution is dispensed into the cartridge (77), following the fluid level upward while dispensing.

The remaining cells are washed out of the sample tube and transferred. 75 ul of system buffer is aspirated into the transfer probe syringe. The buffer is then dispensed into the bottom of the sample tube to wash off any remaining cells that may have been left during the initial transfer. From this, the system buffer is again aspirated and transferred to the sample cartridge (77). In order to cause any bubbles in the cartridge (77) to exit, the volume in the transfer will overfill the cartridge (77), and allow any bubbles to escape through the entry port. Further when dispensing the sample into the chamber, in the presence of a magnetic field supplied by the cartridge device, all magnetically labeled entities within the sample are evenly distributed across the analytical surface of the sample chamber (U.S. Ser. Nos. 10/074,900 and 10/303,309)

The system software writes each sample's data to the cartridge data button. This data includes a flag indicating that the data is now valid and a time-stamp of when the sample was processed.

Motion Control

Overview

At each of the appropriate Stations, improvements in the motion control requirements have been implemented to ensure that during operation, no probe containing a reagent will travel over the opening of another bottle, tube, or cartridge (77). This requirement mitigates potential cross contamination of reagents or samples while on board the system. This requirement is also implemented, in part, by ensuring the position of probes (51) in benign locations during reagent, sample, or cartridge transport movement.

To this end, the process ring (53) positions the sample tubes (54) relative to the magnet assemblies (55), the tube rotation drives, the aspirate and reagent probes (51), the sample tube bar-code reader (56), and the operator. Accurate and precise positioning in the X-axis, is required for the position of the probe tips relative to the sample tubes. This applies both during aspirations, when the probe (51) should typically be well centered in the tube, and for re-suspension reagent dispenses, when the probe (51) should be well aimed at the column of magnetically collected cells. Also, the vertical (Z direction) probe position accuracy and precision is critical at some stations, as this is the basis for liquid level sense accuracy in determining if the proper amount of fluid is in the sample tube at a particular position.

Process Ring—Sample Transport

Factors related to precision, accuracy and step resolution affect the process ring positioning. These include the electro-mechanical drive mechanism and the position sensing system. Proper aspiration and re-suspension will tolerate +/−1.0 mm positioning of the sample tube relative to the probe tip. To this end, the step resolution is specified as not more than 0.25 mm per step.

The process ring drive is designed to move precisely and smoothly at both low and high speeds. After plasma aspiration, the ring can be moved at high speeds, with the acceleration and deceleration profiles that avoid sample disruption in the tubes. A normal one-position move during the batch process, after completion of plasma aspiration, is completed in less than 2.5 seconds. All higher speed half-revolution moves are completed typically in less than 6 seconds.

Carousel—Cartridge Transport

Precise motion control is required for the carousel (57). The carousel positions the cartridge (58) and relative to the transfer probe (51), the cartridge barcode reader, and the operator.

Probe Carriages

The probes (51) have approximately 145 mm of vertical travel, based on the height of the 15 ml sample tube.

Accurate and precise Z-axis vertical positioning of the aspiration and reagent probes (51) in relation to the sample tubes, the reagent bottles, the cartridges and the wash bowls is required as indicated below.

a. During fluid seeks in the sample tubes and the reagent bottles, the probe (51) vertical position assesses the fluid level in the container.

b. During the post-separation aspirations, the aspiration probe (51) follows the fluid level downward, stopping very close to the bottom of the sample tube in order to aspirate the entire contents of the tube.

c. During reagent pickup, the fluid level is followed downward during aspirations while detecting fluid levels and not allowing the probe tip to contact the bottom of the reagent bottles.

d. For re-suspension dispenses, the reagent probe tip is positioned to a height above the target location on the conical tube wall to aim the dispense stream at the column of magnetically collected cells.

e. For the final transfer to the cartridge (77), the probe tip begins near the bottom of the cartridge (77) and follows the fluid level upward during dispensing.

The probe (51) vertical requirements relate directly to requirements on the mechanisms holding the containers mentioned. For example, the process ring and tube holders need to position the tube at a consistent known height for the probe calibration. This imposes constraints on the flatness and tilt of the process ring itself.

Similar requirements apply for reagent transport. Each reagent probe (51) will have a calibrated bottom distance for the reagent bottles. Using only one bottle type for most of the reagents, one bottom calibration is required for all bottles (i.e. 4 ml).

For positioning of the probe tip relative to the bottom of the sample tube, accuracy of +/−0.127 mm is required. This ensures complete fluid removal during post-separation aspirations. To this end, a step resolution for positioning the probe tip relative to the tube or cartridge (77) bottom is achieved in the dual-probe carriage models with the following specifications: 1.8 degree stepper motor (200 steps/rev), 1:1 drive ratio, 12.7 mm lead-screw, 12.7 mm/rev/200 steps/rev=0.063 per step (0.032 mm per half-step).

In order to achieve a full vertical stroke timing of 6 seconds, a 25 mm/sec vertical travel was established.

The X-axis for the aspiration and reagent probes (51) controls the position of the probe tip radially relative to the tubes, the reagent bottles, the cartridges and the wash bowls. During fluid seeks and post-separation aspirations in the sample tubes, the probe radial position is used to center the aspiration probe (51) in the tube. During reagent pickups, the probe radial position is used to center the reagent probe (51) in the reagent bottle. During re-suspension dispenses, the reagent probe (51) is positioned radially to aim the dispense stream at the column of magnetically collected cells on the conical wall of the tube. Then with the final transfer to the cartridge (77), the transfer probe (51) is accurately positioned to center the probe tip in the cartridge chamber opening. For all probe washes, the probes (51) should be well positioned in the wash bowl. These probe radial positioning requirements relate directly to requirements on the mechanisms holding the containers. For example, the process ring must position all 8 tubes consistently relative to the radial position of the probe (51). Similarly, the carousel (57) needs to position all 8 carriers consistently relative to the radial position of the transfer probe (51) at Station 9.

The probe carriages (59) have a 150 mm x-axis stroke, allowing the reagent probe (51) to span the distance from the outer edge of the 15 ml tube to 35 mm in-board on the reagent pack for bottle opening access.

Similar to those mentioned above, factors affecting the probe radial positioning is electromechanical drive mechanism and the position sensing system such as sensors, flags, etc. The most stringent requirement is access for the transfer probe tip into the cartridge chamber opening (1.27 mm diameter probe tip into 2.33 mm diameter opening). This results in about 0.38 mm per side along the probe X travel. The cartridge is accurately positioned within the cartridge holder. The cartridge holder plate is accurately positioned to the mounting surface on the carousel. The probe tip can be repeatedly positioned above the cartridge opening within about +/−0.25 mm. For instrument calibration purposes, the step resolution is not more than +/−0.127 mm.

Magnet Shuttles

The magnet shuttle positions the magnet assemblies relative to the sample tubes and also engages the tube rotation system. For magnetic separations, the magnets are in contact with the sample tube for maximum magnetic field penetration within the sample while separating and for maximum holding force against the tube wall during post-separation aspirations. To maximize the magnetic holding force, the gap between the magnets and the tube must be minimal with any design aspects having no variation due to inaccurate mechanical calibration. In the present invention, custom molded tubes have a thickness specification of 0.89 mm+/−0.127 mm.

All magnets are spring loaded to ensure positive contact with the tubes. The spring-loaded design compensates for variations in concentricity of the tubes and accommodates 0.050" of travel. This spring force is low enough so as to not interfere with tube rotation. The magnet shuttles will have a range of motion of 5 cm, to position the magnets far enough so they don't affect the tube when disengaged and the process ring is indexed.

Positioning of the magnet shuttle is dependant upon the electromechanical drive mechanism and the position sensing system, however, much of the accuracy requirement is mitigated by the spring loading of the magnet shuttles.

Tube Rotators

Tube rotation mechanisms are designed to rotate the tube to facilitate magnetic incubation and separations. For incubations, the tube is rotated relatively quickly when the magnets are retracted. For separations, the tube is rotated very slowly with the magnets engaged, to expose all portions of the tube volume to the high magnetic gradient field and to manipulate the collected cells in a column along the conical wall of the tube that matches the high magnetic field gradient portion of the magnet assembly.

With the primary purpose of the rotation to localize the magnetically collected cells, there are no stringent positioning requirements for the mechanisms. At very slow speeds, a relatively smooth motion is needed to have a reasonably fine step resolution for any motion. For example, a 10 um cell which is sitting against the tube at the highest magnetic gradient point would move abruptly if rotated a large distance. With a small step resolution, the tube is rotated a very small amount whereby the collected cells can gently slide or role to a new high magnetic gradient position.

Fluidics Design

A further embodiment of the present invention is the fluidics design. All fluidic components are placed in a position that would mitigate fluid splashing, spraying and/or spilling on critical mechanical or electrical subsystems. When applicable, drip trays or shields are designed to further mitigate these issues.

System buffer is used as a backing fluid is used for reagent dispenses. When reagents are aspirated into tubing, they coat the tubing and also dilute with the system fluid. By adding a small volume of backing fluid to the dispense volume, residual amounts of the desired reagent, otherwise left on the surface of the tubing, are flushed out to improve the overall recovery of the specific reagent.

Aspiration design guidelines for all parts of the fluidics systems are designed for a range of approximately 50 ul/sec to 1250 ul/sec. The aspiration lines are needed to be primed with system buffer prior to aspiration, allowing for uniform aspiration. To avoid pulsation in the aspiration rate, the pump head must include a sufficient number of rollers. For example, the Cavro Smart Peripump has 8 rollers. The aspiration duration is generally controlled by time or by the pump head rotation. Aspiration probe tips are notched to prevent blocking the tip against the bottom of the sample tube. The typical internal diameter for the aspiration probe tip is 1.27 mm at the probe tip and 1.78 mm in the probe body.

When aspirating fluids after a magnetic separation, the fluid shear forces are minimized as the fluid level drops in the tube. The allowable shear force cannot be calculated since the antigen densities of cells will not be constant. Aspirating the fluid too slowly could potentially cause cells outside the fluid to dry out and stick to the tube wall, thus reducing the ability to recover them. Conversely, aspirating too fast could result in cell loss/damage. Thus, these speeds must be optimized. Optimization depends upon, but not limited to, the magnetic loading of the cells, the magnetic permeability of the ferrofluid particles, the fluid meniscus velocity during aspiration washes, the proximity of the probe tip to the magnetically held cells and the magnetic field gradient holding the cells in place.

The aspiration design specifications for the waste aspiration subsystem are set to aspirate at nominal rate settings from approximately 50 ul/sec to 1250 ul/sec. Following a post-separation aspiration, the residual volume in the tube is less than about 6 ul.

Waste Aspiration

The waste aspirations encompass plasma aspiration, most post-separation aspirations and probe washing. In most instances these aspirations are performed with a peristaltic pump, through a series of pinch valves. This type of pump and valves control fluid flow, however, do not com in contact with the fluid itself. This avoids degradation of fluidic components that are sensitive to contact with biological materials.

Plasma aspiration is performed in two steps after the red cell layer is detected by the system. First, the majority of the plasma is aspirated (about 450 ul/sec) using the peristaltic pump down to about 1.5 to 2 ml of the remaining plasma. Second, the peristaltic pump is slowed to aspirate at about 110 ul/sec, removing an additional 1 ml and leaving approximately 0.5 ml of plasma in the tube. The slower speed is used to minimize turbulence in the sample when the probe tip is near the region of the sample that contains the target cells.

Probe Washing

Probe washing is another aspect of fluidics design and consists of pulling system fluid through the aspiration probe (51) or the washbowl. When washing probes (51) or draining the washbowls, the pump is operated at a fairly high rate (1 ml/sec). A technique for washing the outside of the probes (51) involves building a vacuum with the peristaltic pump while energizing (closing) a pinch valve. Releasing the pinch valve causes a rapid aspiration of fluid from the washbowl and improves the probe washing of the outer surface of the probe (51) due to a high meniscus velocity within the wash bowl.

Reagent Dispense

Reagent additions to a sample tube are performed at Stations 1, 4, 5, 7 and 9. Some of these additions are for re-suspensions, using from 150 ul to 3 ml.

Reagent probe tips for dispenses are designed to achieve reasonable stream velocity. Typically, the internal diameter at the tip is approximately 0.9 mm to 1.27 mm, depending upon the probe design. Variations in the inside diameter of the dispense probe tip will dramatically change the fluid velocity exiting the probe tip.

The reagent dispense at Station 1 is a large volume dispense of 6.3 ml. Using the Cavro XD 1000 pump the maximum syringe size is 5 ml. The operation requires 2 dispense cycles with a buffer volume of greater than 5 ml. The dispense speed for this step is sufficient to mix the red cells and mix the buffer, the ferrofluid and capture enhancing reagent.

At Station 4, 3 ml of wash solution is dispensed. This consists of a combination of wash dilution buffer and system buffer to make up 3 ml. Station 4 is a re-suspension dispense whereby a fluid stream from the probe (51) is aimed at the collection cells on the wall of the sample tube.

Station 5 dispenses a final volume of 650 uL. At Station 7, a 650 to 800 uL mixture of system buffer and wash dilution buffer are added. After this dispense, cell settling for ferrofluid reduction begins.

Station 9 dispenses 150 ul of stabilizing reagent after the removal of unbound ferrofluid. The system may perform an aspirate and dispense as a mixing step after the initial dispense in order to ensure that cells are uniformly suspended in solution.

The transfer probe (51) is necked down to 1.27 mm for 40 mm so the probe tip can get into the 2.33 mm diameter opening in the cartridge and reach to the bottom of the 30 mm analysis chamber. The transfer probe (51) is Teflon coated on the outside surface to minimize cell carryover. Transfer probe (51) wash sequence is designed to a carryover specification that is less than 2 cells in 50,000.

Sensor System Design

Overview

Further improvements are found in the design of the sensor system which is used to ensure process integrity. The process steps include plasma aspiration, magnetic separations, post-separation aspirations, reagent additions and final transfer to the cartridge, among others. Because the most severe error possible would be processing the sample incorrectly, the system needs to automatically verify that these steps are properly executed. In some cases, failure to do so results in an abnormal final result for the sample such as an incorrect cell count because of an incorrect cell capture or incorrect cell labeling. In other cases, an improperly executed step results in a biohazard condition in the instrument such as a failure to aspirate following the reagent addition and the loss of one or more samples. The sensor system is used to verify that all samples are processed correctly. Once a reagent is added to the sample, the sample is committed to completion.

Bulk Fluid Sensing

The system fluid is used for priming and washing the probes (51) in the system. It may also be used as rbacking fluid for probe tubing and as a reagent itself. As described in earlier sections, sensors are employed to verify at the start of the run that there is sufficient system fluid to complete the run. Loss of fluid during the run results in a loss in the maintenance of the proper priming of the fluid-backed probes (51). This results in incorrect reagent volumes, and an inability to properly wash the probes (51).

Analog sensing is used to measure the weight of the bottle periodically during operation of the instrument. Software estimates the amount of fluid required during the run based upon general priming requirements, the test definition information and the number of samples to be run. With the start of a run, the system determines if there is enough to complete the run. Otherwise, the run is disabled until the operator replenishes the fluid.

The system estimates the worst-case fluid usage, based upon the user entered batch size, and multiplies by the number of samples to be run with the calculation including the initial system priming and probe washing.

Waste Sensing

There is a further sensing requirement for liquid waste. The analog sensing is similar to that described for the system fluid sensing. Here, the sensor is used to verify that there is enough capacity at the start of the run, and that the bottle does not become full during the run. As an option, a liquid waste line to a laboratory drain can be used. Capacity in the waste bottle for the liquid waste includes waste from priming and washing probes, as well as the liquid waste aspirated from the sample tubes. The waste bottle itself is sized to allow for waste containment for multiple batches of samples.

A sensor is used to mitigate against running out of liquid waste capacity, in which case probe priming, probe washing and general aspirations are stopped and the run is aborted. A sensor is used during maintenance activities, such as a daily cleaning procedure.

Data Button and Barcode Sensing

The device acts as both a sample cartridge holder as well as a device that introduces a magnetic field to the sample as it is dispensed into the cartridge. With respect to the sample cartridge component, the cartridge is loaded onto the machine. A data button, located in the cartridge holder, is used to transfer information, written by the system's software, regarding the sample to the imaging system. The data button contains a unique ID for traceability.

The cartridge itself is serialized and has a barcode which enables the system to identify the cartridge ID. The instrument reads the barcode in order to detect that a cartridge is installed in the cartridge holder. The system provides an access door to the carrousel for safety and prevents operator access while the carousel is moving.

The cartridge carousel has 8 positions. The cartridge/holder is positioned at the operator access position, at the data-button/bar-code read position and at the transfer probe position (Station 9). The system must know that the correct cartridge is in proper position. The carousel utilizes a sensor arrangement that identifies each position on an absolute basis.

When the cartridge/holder is loaded onto the cartridge carousel, its presence is verified by reading the embedded data-button. The system verifies that the cartridge is new and has not been previously used on the instrument by comparing the serial number with the instrument database of previously scanned cartridges.

The data button embedded in the cartridge/holder is used to transfer data regarding the sample to the imaging platform. Data is written to the cartridge/holder at the time of the sample dispense into the cartridge. Typical data includes sample information, reagent lot information, test performed, rejection information, and other relevant information. The data button connections are made to each cartridge/holder.

Reagent Pack Sensing

The primary reagents are loaded onto the instrument in a single reagent pack (52). The reagent pack area is in the middle of the process ring. The probes travel above the ring and the reagent pack. The pack contains 1 bottle for a wash dilution buffer and 6 small bottles for other reagents required for the process. The design of the pack is intended to position the bottles in a radial fashion for probe access during operation of the system. During a batch run, the reagent carousel positions the appropriate bottle at each probe (51) station when required for reagent aspiration. The software maintains the position of the reagent carrier and schedules probe access to the requested bottle in order to service all probes simultaneously.

The reagent carousel positions itself in one or more load positions for the operator to load or unload reagents. During a run, the carousel (52) positions the appropriate reagent bottle at a probe (51) station for reagent aspiration, making it essential to position the correct reagent bottle be positioned at the probe (51) for reagent access. The sensors are designed to allow for absolute reagent pack positioning. The reagent data button, described earlier, contains general information regarding the reagents such as, but not limited to, lot number, expiration date, etc. for use in inventory control. When a reagent is aspirated, the data button will decrement the amount of reagent left in the pack. In this manner if the pack is removed from the instrument for any reason (i.e. refrigerated storage), the instrument knows the remaining volume the next time it sees the pack. Thus, the data button may be used for lot control, on-board time tracking and expiration dates.

Red Cell Sensing

As described earlier, the operator loads the tubes with centrifuged blood samples directly onto the process ring. Each entry requires the operator to press a button whereby the system indexes the ring to the next position. This process is repeated for the number of tubes indicated by the operator. The system reads the tube's bar-code label and detects the red cell layer position in each sample tube prior to loading the next tube. For this process, the barcode reader is located at the next position after the tube loading position. A ccd camera is used to sense the red cell layer in the sample. The system uses the presence of a barcode label and/or red cells as a means for tube detection. The system will not process a batch of samples if a sample's red cell layer is not detected.

The location of the transition from red cells to plasma varies by patient hematocrit and the original sample volume. Thus, it is important to measure the location of the red cell layer in order to know how much plasma to remove. Normal hematocrit levels range from 45 to 52% for adult men and 37 to 48% for adult women. Assuming a hematocrit range of 20 to 60% for a 7.5 ml sample, results in a physical range of 1.5 to 4.5 ml of red cells in a 7.5 mL centrifuged, whole blood sample.

The system removes all but about 0.5 ml of plasma, without disturbing the cells in the buffy coat layer. To do this, red cells, which absorb light in the 532 nm region, is illuminated with green LED light (532 nm). A CCD camera captures an image of the illuminated tube. Under these lighting conditions, the demarcation of the red cell layer is of high contrast with that of the plasma layer. An image analysis algorithm is applied to the image to determine where the transition of red cells and plasma occurs.

One embodiment of the algorithm in the present invention involves calculations of pixel intensity to locate the red cell layer based upon the following steps after image capture:
1—create first derivative by subtracting previous pixel value from current pixel value.
2—create second derivative by subtracting previous pixel value from current pixel value.
3—average over five (5) pixel ensemble by averaging the sample and it's four nearest neighbors.
4—plot original data, first derivative and second derivative.
5—the location of the largest zero crossing of the second derivative is the location of the red cell layer.

The location of the transition is used for plasma aspiration. The system senses the transition between plasma and red cells with an accuracy of +/−0.25 mm.

Pump Sensing

Syringe Pumps

The syringe pumps include error detection for sensing improper movement of the piston, which results in an incorrect volume of reagent aspirated and dispensed. Additionally, the syringe pumps include overload detection. The syringe pumps include an integral valve with sensors able to detect errors related to the valve operation.

Peristaltic Pumps

The peristaltic pumps include error detection for faults such as, but not limited to, the pump head not moving, or the pump head moving in the wrong direction. This provides only partial protection against a failure to aspirate. For example, failed pinch valve or pump tubing would also create a gross failure. Fluid sensing, described earlier, is designed to mitigate failure modes that the pump cannot detect.

Fluid Level Sensing

A critical sensing function is ensuring the proper reagent volumes are added to the tubes. All reagent additions are followed by fluid level sensing to ensure that the proper volume of reagents was added from the previous step.

The reagent probes (51) are used to aspirate fluid from reagent bottles and dispense them into the sample tube. The reagent probe (51) at Station 9 is also the 'transfer probe' that transfers the final product to the cartridge. At most stations, the reagent probe (51) is performing a 'resuspension' dispense, to resuspend cells that have been magnetically collected on the wall of the tube.

The primary purpose of reagent probe level sensing is to detect the presence of fluid in the reagent bottle being accessed and in the sample tube after reagent is dispensed. The typical reagent bottle aspiration sequence would be:
 a. position the reagent bottle at the probe station,
 b. seek fluid,
 c. aspirate the required volume while moving the probe (51) downward to follow the fluid level.
 d. seek fluid after aspiration
 e. calculate the change in fluid level and determine if the reagent pick-up was successful Magnet Position Sensing The magnet shuttle positions the magnets close to the tube during separations and magnetic incubations. The magnets are retracted away from the tube during cell re-suspension dispenses and when indexing the process ring. The magnet shuttle also engages the tube rotation motor. Engagement of the tube rotation motor occurs with a different magnet shuttle position. For example, at Station 2 and 3, motor engagement occurs when the magnet shuttle is disengaged. At Station 4, the motor engagement occurs when the magnet is engaged. The engagement mechanism allows adjustment of the engagement position. The mechanism includes a home sensor, activated when the magnet shuttle is retracted. The system monitors motor step counts relative to home position to ensure proper magnet positioning during the process.

Tube Rotation Sensing

During magnetic incubation and separations, rotation of the tube is necessary in order to fully collect the labeled cells and position them for subsequent re-suspension after the post-separation aspiration. The instrument senses that the tube cup is rotating by means of an optical sensor and flag arrangement at the bottom of the tube holder. A knurled feature on the tube holder cup, the spring load force of the tube holder along with features on the tube itself, generates enough friction to ensure tube rotation.

Magnetics Design

Figure 7:
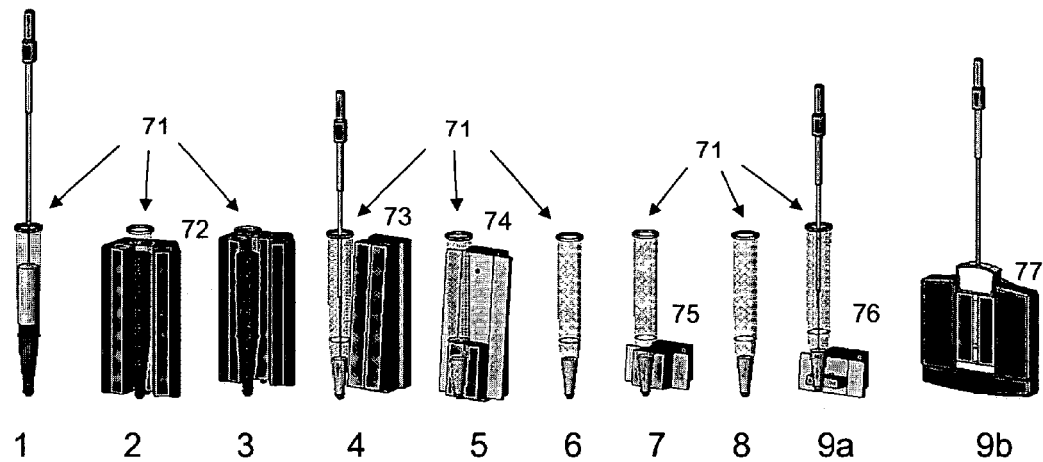
FIG. 7: Sequential effects on the sample at individual stations. Station 1 aspirates the plasma and adds capture reagent. Station 2 and 3 is magnetic incubation. Station 4 is the primary magnetic separation and resuspension portion. Station 5 is the addition of staining reagent. Station 6 is the incubation of staining reagent. Station 7 is the magnetic wash. Station 8 is the first step in unbound magnetic particle removal. Station 9 is the second step in unbound ferrofluid removal as well as the final resuspension and sample transfer to the cartridge.

FIG. 7 shows the samples at each station (1-9) and the associated magnetic design.

The probes are constructed from Inconel alloy rather than stainless steel because of the non-magnetic properties of Inconel. Inconel is a nonmagnetic, corrosion and oxidation-resistant, nickel-base alloy, typically used for heat shields, furnace hardware, and gas turbine engine ducting. Inconel has a magnetic permeability of 1.000 and is therefore not magnetic in the presence of strong magnetic field gradients.

Station 2 and 3—Magnetic Incubation. For Station 2 and 3, the goal of the magnet (72) is to pull the ferrofluid particles across the diameter of the tube (71) to improve collisions between target cells and magnetic particles. The magnetic field causes the particles to form 'chains' as they pass through the sample. This further improves collisions and subsequent cell binding. The incubation magnets (72) used for Stations 2 and 3 are in a Tripole format with a 70 degree angle between the north-south-north or south-north-south magnets.

The magnet configuration is an improvement of the previously described quadrupole configuration (U.S. Pat. Nos. 5,186,827 and 5,466,574). Since the magnet (72) is required to be engaged and disengaged from the sample, the magnet has an open side to allow the sample to be placed in and out of the magnetic field. In previously described quadrupole configurations, the sample tube is required to be removed from the magnet vertically. This makes automation difficult.

Station 4—Separation

Station 4 magnetic separation is designed to separate the ferrofluid coupled cells from the sample and concentrate the cells in a location that is re-suspended with a 3 ml fluid stream. The Station 4 magnet (73) is designed as a slanted dipole magnet with a 180 degree angle between the north and south facing magnets. The slant of the magnet matches the angle of the cone portion of the sample tube to provide both a gradient vector towards the side of the tube as well as a gradient vector towards the bottom of the tube. This configuration is designed to bring cells to the wall of the tube at or below the 3 ml mark of the tube to allow for subsequent re-suspension of the cells after aspiration. In this configuration, field gradients in access of 20 Kgauss/cm are present at the inside tube wall. This improvement exceeds the field gradients found in prior quadrupole designs.

Station 5—Magnetic Wash

The goal of the Station 5 magnet is to separate the magnetically labeled cells that have been re-suspended in 3 ml of protein based buffer at Station 4. The magnet (74), along with the tube rotation serves to position the cells at a specific place on the tube wall prior to re-suspending the cells with permeabilization reagent (U.S. Ser. No. 10/780,349) and staining reagents. The magnet design for Station 5 is a slanted dipole configuration, similar to Station 4. Here, the magnets (74) are shorter due to the lower sample volume. The magnet (74) is angled to provide both a horizontal and downward magnetic force on the cells since the cells are re-suspended with a smaller volume than 3 ml. The re-suspension volume is between 650 and 800 ul.

Station 7—Magnetic Wash

The magnet design for Station 7 is similar to the magnet design for Station 5. The size of the magnet (75) is shorter than that used at Station 5 due to the decreases reagent dispense volume.

Station 9—Ferrofluid Fractionation

The goal of the magnet design for Station 9 is to capture cells that have settled in the sample tube over an approximate 20 minute period (at Station 8). The density of the fluid at this stage is expected to be approximately 1.01 gm/ml (note: The cells are expected to have a density between 1.06 and 1.08 gm/ml.) The cells are captured at a point above the bottom of the conical bottom of the tube. This allows the probe (51) to aspirate all the residual liquid that contains the unbound ferrofluid and other reagents while leaving the cells intact.

For Station 9, the magnet design is a Dipole with 180 degree angles between poles. The shape of the magnets (76) allows contact with the outside of the tube at a preset vertical position. The magnetic field strength is sufficient to attract and hold cells in close proximity to the poles, but not strong enough to attract unbound ferrofluid in solution (note: all metallic components used to hold the tube in place near the bottom of the tube are required to be non-magnetic. The magnets, along with the protocols for the control of settling time, magnet engagement time, aspiration height and aspiration speed are optimized for both ferrofluid removal and minimal cell loss.

Computer Interfaces

The host computer hardware interfaces for the instrument have been designed for easier operation. The keyboard is less than 18" (46 cm), allowing enough space to support other languages in addition to English. The function keys have a minimum of 10 function keys along the top. The keyboard can be easily stored under the instrument. The display is a flat panel, SVGA Color with greater than 60 degree viewing angles. Embedded in the front of the instrument, the display has a 8.5" diagonal size. 6 buttons are mounted along the bottom of the display. An optional mouse can be used during instrument development or a service call. The instrument has an IDE hard drive with 20 GB or larger of storage. An integral RW CDROM drive is supplied with the system, and functions for software updates, back-up and restore functions. The printer is used for run reports, calibration lists, etc. The printer uses 3" thermal paper with a cutting feature. There are 4 serial ports available; 1 for barcode reading, 1 for an external modem, and 2 for the data button readers. Door sensors are used to verify the doors are closed prior to initiating a run or cleaning procedure. Sensors are used to detect the opening of the process area door. The sensors are monitored by firmware and software.

The host computer monitors the temperature of the internal areas periodically with an accuracy of +/−degree Celsius. Of the two sensors used, one is inside the sample processing area, and the other assesses the ventilation fan for the electronics.

Reagent Packaging

The reagent packaging has been developed to support the rapid and error-free instrument design. The bulk fluids include a system backing fluid and diluted bleach solution used for system cleaning. The bulk containers are filled with specific bulk reagents or liquids according to instructions. The bulk containers are designed to be reusable with instructions for periodic cleaning of the bottles. The reagent pack consists of a disposable reagent holder, reagent bottles, integral data button and a reusable reagent pack carrier that is supplied with the instrument. Reagent bottles are industry standard bottles, but can be replaced with custom bottles having similar shape and size. The reagent pack carrier is designed to fit into a carrier, subsequently placed onto the instrument. The carrier is re-useable after the reagent pack has been depleted. The carrier also provides electrical connections for the grounding connections required for capacitive levels sensing of individual bottles in the reagent pack and for the data button connection for reading and writing to the reagent pack data button. The carrier provides a means for holding the individual bottles, allowing for the caps to be removed with only one hand of the operator. Further, an evaporation cover can be optionally applied to a reagent pack in the re-usable carrier for storage in a refrigerator between uses.

System Cleaning

In order to prevent the biological growth and protein build-up experienced in most liquid-based chemistry instruments, the system design has been implemented to facilitate automated periodic cleaning. The recommended cleaning solution is a bleach solution (5% Sodium Hypochlorite) commonly found in laboratories. The automated cleaning procedure is defined by the following:

1—Completely prime the system with cleaning solution.
2—Allow a dwell time for the cleaning agent to cleanse the tubing.
3—Dry prime the system to remove as much cleaning solution as possible.
4—Flush the dry lines with de-ionized water or system fluid.
5—Re-prime the system with the normal system fluid.

The entire cleaning system is designed to be a 'walk away operation' meaning that, unlike the cleaning procedures of prior inventions, the apparatus of the present invention requires no operator intervention once initiated.

It is to be understood and appreciated that these improvements are only illustrative of the many additional potential applications of the apparatus and method that may be envisioned by one of ordinary skill in the art, and thus are not in any way intended to be limiting of the scope of the invention. Accordingly, other objects and advantages of the invention will be apparent to those skilled in the art from the following detailed description, together with the associated claims.

We claim:

1. A device for processing biological samples suspected to contain rare target bioentities comprising;
   a. one or more carriers for receiving and transporting vessels containing said biological samples;
   b. one or more carriers for receiving and transporting vessels containing reagents;
   c. one or more vessels containing bulk system fluid;
   d. one or more fluidic pumping means for manipulating said biological sample and said reagents wherein said pumping means has an aspiration rate between 120 ul/sec to 250 ul/sec to prevent damage to said rare target bioentites linked to paramagnetic particles;
   e. one or more magnetic separators incorporating a tube rotation system
   f. at least one magnetic incubator having a 70-degree tripole configuration; and
   g. one or more programmable controlling means capable of storing and executing commands to control various system components wherein at least one command requires backfluid flushing when aspirating and dispensing said reagents.

2. The device of claim 1, further comprising one or more electronic means capable of tracking reagent inventory.

3. The device of claim 1, further comprising one or more electronic means capable of tracking reagent inventory.

4. The device of claim 1, further comprising one or more electronic means for tracking sample identification.

5. The device of claim 1, wherein said fluidic pumping means includes one or more non-magnetic alloy probes connected to a pump where said probes are positioned within said vessels using capacitive liquid level sensing and wherein said probes contain small air gaps when used in multiple pick-up methods.

6. The device of claim 5, further comprising one or more washing means for washing said probes after contacting said biological sample or said reagents.

7. The device of claim 1, wherein said magnetic separators create a holding force within said vessels containing said biological samples that is greater than shear forces experienced by aspiration of said biological sample from said magnetically collected target bioentity during processing.

8. The device of claim 7, wherein said magnetic separators create a downward force in addition to said holding force in order to vertically concentrate said magnetically collected target bioentity.

9. The device of claim 8, further comprising a means for rotating said vessels containing said biological samples while subjected to magnetic forces order to concentrate said magnetically collected target bioentity.

10. The device of claim 1, wherein said magnetic separators create lateral forces capable of moving magnetically responsive entities through said biological sample.

11. The device of claim 10, wherein moving said magnetically responsive entities through said biological sample enhances labeling of said entities 12. The device of claim 1, wherein said target bioentites are selected from a group consisting of epithelial cells, tumor cells, endothelial cells, fungal cells, bacterial cells, cellular debri, cellular components, and combinations thereof.

13. The device of claim 1, wherein said processing is in preparation of diagnostic image analysis, diagnostic nucleic acid analysis, and combinations thereof.

* * * * *